United States Patent [19]

Nielsen et al.

[11] Patent Number: 4,935,544
[45] Date of Patent: Jun. 19, 1990

[54] POLYNITROBIPHENYL DERIVATIVE

[75] Inventors: Arnold T. Nielsen, China Lake; Ronald L. Atkins; William P. Norris, both of Ridgecrest, all of Calif.

[73] Assignee: The United States of America as represented by the Secretary of the Navy, Washington, D.C.

[21] Appl. No.: 171,919

[22] Filed: Jul. 17, 1980

[51] Int. Cl.$^5$ .................... C06B 25/04; C07C 87/50; C07C 79/10
[52] U.S. Cl. .................... 564/309; 568/931; 149/105
[58] Field of Search ................ 564/309; 568/931; 149/105

[56] References Cited

U.S. PATENT DOCUMENTS

| | | | |
|---|---|---|---|
| 982,509 | 1/1911 | Laska | 564/309 |
| 3,320,320 | 5/1967 | Kamlet et al. | 149/105 |
| 3,402,202 | 9/1968 | Hein et al. | 568/901 |
| 3,403,185 | 9/1968 | Nilsson et al. | 149/105 |
| 3,574,758 | 4/1971 | Shipp et al. | 149/105 |
| 3,886,173 | 5/1975 | Dacons et al. | 568/931 |
| 3,941,812 | 3/1976 | Gilbert | 149/105 |
| 3,985,595 | 10/1976 | Benziger | 149/105 |
| 4,032,377 | 6/1977 | Benziger | 149/105 |

OTHER PUBLICATIONS

C.A., vol. 69, 39405k (1968).
C.A., vol. 58, 10169f (1963).
C.A., vol. 91, 59620j (1979).
C.A., vol. 84, 92352b (1976).
C.A., vol. 16, 1238$^1$ (1922).
C.A., vol. 7, 1355$^3$ (1913).

*Primary Examiner*—Teddy S. Gron
*Attorney, Agent, or Firm*—Sol Sheinbein; Melvin J. Sliwka

[57] ABSTRACT

This invention illustrates a new compound, octanitrobenzidine. It is utilized as a new high energy explosive compound. Octanitrobenzidine is formed by dissolving a tetrqanitrobenzidine with sulfuric acid in the presence of a metal sulfate catalyst. This reaction mixture is further reacted with nitric and sulfuric acid at a temperature sufficient to complete the reaction, then rapidly cooled, and octanitrobenzidine is recovered.

7 Claims, No Drawings

POLYNITROBIPHENYL DERIVATIVE

BACKGROUND OF THE INVENTION

1. Field of the Invention

This invention relates to a new compound and more particularly to a new compound useful as a high energy explosive. This invention further relates to a method for preparing a new compound, namely, a polynitrobiphenyl derivative. More specifically, this invention relates to a method for the preparation of octanitrobenzidine.

2. Description of the Prior Art

Aryl compounds with large numbers of nitro groups on the rings are well known as explosives. In ordnance it is desirable to maximize explosive power and minimize sensitivity to shock and impact. These properties are especially important where personnel are in close proximity to such ordnance as in ships, aircraft, armored vehicles, etc. where there is a high probability of shock from bullet or fragment impact. Trinitrotoluene, commonly known as TNT, and triaminotrinitrobenzene, known as TATB, are high energy explosives used in ordnance. TNT has the disadvantage of being too sensitive to shock and not sufficiently powerful; whereas TATB is too insensitive to shock but more powerful than TNT. TATB has added disadvantages of having a large critical failure diameter and being difficult to purify.

SUMMARY OF THE INVENTION

According to this invention, a new compound, octanitrobenzidine is created. Further, a method to prepare this compound is disclosed. This method consists essentially of dissolving a tetranitrobenzidine and metal sulfate catalysts in concentrated sulfuric acid. This mixture is further reacted with a solution of sulfuric and nitric acid at an elevated temperature. After sufficient cooling, the product is filtered washed and dried. Octanitrobenzidine, a new explosive compound is more sensitive to impact than TATB and less sensitive to impact than TNT, but has more explosive power than either.

DESCRIPTION OF THE PREFERRED EMBODIMENT

Tetranitrobenzidine, a known compound, and a metal sulfate catalyst such as lead sulfate or copper sulfate, are dissolved in concentrated sulfuric acid. This method is also feasible without the catalysts but the yield and purity are decreased slightly. This mixture is reacted with a solution of sulfuric and nitric acid. This reaction mixture is held at an elevated temperature for a period of time during which the nitration of tetranitrobenzidine occurs. The resultant reaction mixture is cooled and the solid separated by filtration. The solid is washed using sulfuric acid and aqueous hydrochloric acid. The product is subsequently dried. The yellow-orange crystals are octanitrobenzidine.

The manner of carrying out this method will be clearer from the following example. It being understood that the scope of the invention is not to be limited thereby.

EXAMPLE I

In a preparation without the use of catalysts, 50.0 g. of 2,2',6,6'-tetranitrobenzidine is dissolved in 2000 ml. of 100% sulfuric acid ($H_2SO_4$). After a sufficient period of time for dissolving the reactants, an acid mixture containing 130 ml. of 90% $HNO_3$ and 200 ml. of 96% $H_2SO_4$ is added. While stirring, this mixture is heated rapidly to 70° C. and held at that temperature for a period of time from about 1 hour to about 2.5 hours. This reaction mixture is then cooled rapidly to 0°–25° C. and stirred for a period of time from about 0.5 hour to 2 hours. This mixture is filtered and the solid is washed successively with concentrated $H_2SO_4$, 50% $H_2SO_4$, and 1N aqueous HCl. This product is then dried to yield 47.8 g. of octanitrobenzidine.

EXAMPLE II

In a typical preparation, 50.0 g. of 2,2',6,6'-tetranitrobenzidine is dissolved in 2000 ml. of 100% sulfuric acid ($H_2SO_4$) containing 1.0 g. of $PbSO_4$ and 1.0 g of $CuSO_4$ as catalysts. After a sufficient period of time for dissolving the reactants, an acid mixture containing 130 ml. of 90% $HNO_3$ and 200 ml. of 96% $H_2SO_4$ is added. While stirring, this mixture is heated rapidly to 70° C. and held at that temperature for a period of time from about 1 hour to 2.5 hours. This reaction mixture is then cooled rapidly to 0°–25° C. and stirred for a period from about 0.5 hours to 2 hours.

The yellow-orange reaction mixture containing partially crystallized octanitrobenzidine is then isolated with normal filtering. This product is washed successively with concentrated $H_2SO_4$, 50% $H_2SO_4$, and then 1N aqueous HCl. This product is then dried to yield 48.8 g. (65.4% yield) of octanitrobenzidine. It is then crystallized from acetonitrile or ethyl acetate.

Formula:

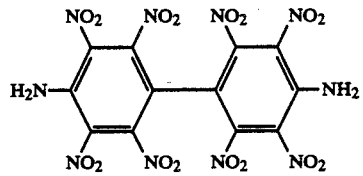

Yellow-orange needles
Molecular formula = $C_{12}H_4N_{10}O_{16}$
Molecular weight = 544.23
Nitrogen percentage = 25.74% N
Oxygen balance to CO and $H_2O$ = −29.4
Density = 1.82 g/cm$^3$
Impact sensitivity = 95 cm (2.5 Kg weight)
Melting point = 280°–290° C. (unrecrystallized)
Melting point = 310° C. (recrystallized from acetonitrile)
Detonation velocity (calc'd) = 8300 m/sec.
Detonation pressure (calc'd) = 317 kbar Octanitrobenzidine may be utilized as an explosive in the same manner that other solid, crystalline explosive materials are utilized.

What is claimed is:

1. Octanitrobenzidine.

2. A method of preparing octanitrobenzidine comprising the steps of:
   A. dissolving 2,2',6,6'-tetranitrobenzidine in sulfuric acid to form a solution;
   B. reacting the solution with a mixture of sulfuric acid and nitric acid;
   C. heating a reaction mixture for a period of time sufficient to complete the reaction; and
   D. recovering octanitrobenzidine.

3. A method as in claim 2, wherein the 2,2',6,6'-tetranitrobenzidine is dissolved in the sulfuric acid of step A in the presence of a metal sulfate catalyst selected from the group consisting of lead sulfate and copper sulfate.

4. A method as in claim 2, wherein said heating is at a temperature from about 60° C. to about 80° C.

5. A method as in claim 8 wherein said heating is carried out for a period of time of from about 1 hour to about 2.5 hours.

6. A method as in claim 2 or 9, wherein the heating is followed by rapid cooling to 0° C.-25° C. and holding it in that temperature range for a period of time from about one half hour to about 2 hours.

7. In a method for creating an explosion comprising the steps of providing an explosive compound and detonating said compound, the improvement residing in utilizing octanitrobenzidine as said compound.

* * * * *